US009205036B2

(12) United States Patent
Karlinsey

(10) Patent No.: US 9,205,036 B2
(45) Date of Patent: Dec. 8, 2015

(54) DENTAL COMPOSITION

(71) Applicant: Robert Karlinsey, Indianapolis, IN (US)

(72) Inventor: Robert Karlinsey, Indianapolis, IN (US)

( * ) Notice: Subject to any disclaimer, the term of this patent is extended or adjusted under 35 U.S.C. 154(b) by 265 days.

(21) Appl. No.: 13/767,173

(22) Filed: Feb. 14, 2013

(65) Prior Publication Data

US 2014/0056827 A1    Feb. 27, 2014

Related U.S. Application Data

(63) Continuation-in-part of application No. 12/465,330, filed on May 13, 2009, and a continuation-in-part of application No. 12/507,989, filed on Jul. 23, 2009, said application No. 12/465,330 is a continuation-in-part of application No. 11/701,210, filed on Jan. 31, 2007, now abandoned, said application No. 12/507,989 is a continuation-in-part of application No. 11/701,210, application No. 13/767,173, which is a continuation-in-part of application No. 12/018,627, filed on Jan. 23, 2008, now Pat. No. 8,556,553.

(60) Provisional application No. 60/888,354, filed on Feb. 6, 2007, provisional application No. 60/891,849, filed on Feb. 27, 2007, provisional application No. 60/941,095, filed on May 31, 2007.

(51) Int. Cl.
| | |
|---|---|
| A61K 9/68 | (2006.01) |
| A61Q 11/00 | (2006.01) |
| A61K 8/02 | (2006.01) |
| A61K 8/21 | (2006.01) |
| A61K 8/55 | (2006.01) |
| A61K 8/24 | (2006.01) |
| A61K 8/19 | (2006.01) |
| A61K 8/362 | (2006.01) |
| A61K 8/46 | (2006.01) |
| A61K 8/11 | (2006.01) |
| A61K 9/00 | (2006.01) |
| A61K 9/08 | (2006.01) |

(52) U.S. Cl.
CPC ............ *A61K 8/24* (2013.01); *A61K 8/0216* (2013.01); *A61K 8/11* (2013.01); *A61K 8/19* (2013.01); *A61K 8/21* (2013.01); *A61K 8/362* (2013.01); *A61K 8/463* (2013.01); *A61Q 11/00* (2013.01); *A61K 9/0063* (2013.01); *A61K 9/08* (2013.01); *A61K 2800/92* (2013.01)

(58) Field of Classification Search
CPC .... C04B 22/064; C04B 28/34; C04B 40/065; C04B 20/107; C04B 14/28; C04B 14/366; C04B 12/025; C04B 14/305; C04B 24/2641; C04B 28/344; C04B 20/1077; C04B 28/342; C04B 40/06; C04B 14/06; C04B 2111/00836; C04B 22/10; A61K 6/0038; A61K 6/097; A61K 8/24; A61K 6/0017; A61K 8/0216; A61K 8/19; A61K 8/21; A61K 8/362; A61K 6/033; A61K 2800/52; A61K 2800/92; A61K 47/02; A61K 47/36; A61K 6/0082; A61K 6/0675

See application file for complete search history.

(56) References Cited

U.S. PATENT DOCUMENTS

| | | | |
|---|---|---|---|
| 3,190,568 A | 6/1965 | Freedman et al. | |
| 3,876,160 A | 4/1975 | Bloch | |
| 4,018,619 A | 4/1977 | Webster et al. | |
| 4,677,140 A | 6/1987 | Shioitsu | |
| 4,877,603 A | 10/1989 | Degenhardt et al. | |
| 5,053,212 A | 10/1991 | Constantz et al. | |
| 5,342,441 A | 8/1994 | Mandai et al. | |
| 6,053,970 A | 4/2000 | Ison et al. | |
| 6,126,097 A | 10/2000 | Chen et al. | |
| 6,334,583 B1 | 1/2002 | Li | |
| 6,491,900 B2 * | 12/2002 | Chow et al. | ...... 424/57 |
| 6,840,961 B2 | 1/2005 | Tofighi et al. | |
| 2002/0037258 A1 | 3/2002 | Dodd et al. | |
| 2003/0069638 A1 | 4/2003 | Barlow et al. | |
| 2003/0120351 A1 | 6/2003 | Tofighi | |
| 2003/0124066 A1 | 7/2003 | Dixon, Jr. et al. | |
| 2003/0199615 A1 | 10/2003 | Chaput et al. | |
| 2004/0101494 A1 | 5/2004 | Scott et al. | |
| 2004/0126335 A1 | 7/2004 | Faller et al. | |
| 2005/0084461 A1 | 4/2005 | Winston et al. | |
| 2006/0175443 A1 | 8/2006 | Bysouth | |
| 2007/0149650 A1 | 6/2007 | Masuda | |

(Continued)

FOREIGN PATENT DOCUMENTS

| | | |
|---|---|---|
| CA | 1089428 | 11/1980 |
| FR | 2594130 | 8/1987 |

(Continued)

OTHER PUBLICATIONS

Schemehorn, et al., "Comparison of Fluoride Uptake into Tooth Enamel from Two Fluoride Varnishes Containing Different Calcium Phosphate Sources", The Journal of Clinical Dentistry, vol. 22, No. 2, 2011, pp. 51-54, http://premusa.com/Downloadablefiles/JCD_22_2_Schemehorn_et-al.pdf; entire document.

Walsh, "Evidence that demands a verdict: latest developments in remineralization therapies", Australasian Dental Practice, 2009, pp. 49-59, http://geriatricdentistry.com/wp/wp-content/uploads/2011/08/L.-Walsh-remin.article.pdf; p. 50, col. 2, paragraph 2; p. 51, col. 2, paragraphs 2-3, col. 3, paragraph 1.

(Continued)

*Primary Examiner* — Audrea Buckley
(74) *Attorney, Agent, or Firm* — C. John Brannon; Brannon Sowers and Cracraft PC

(57) ABSTRACT

Aqueous homogeneous oral care compositions including a fluoride salt and unfunctionalized β-tricalcium phosphate, characterized in that β-tricalcium phosphate is present in a catalytic and fluoride-stable amount relative to the fluoride salt. Such compositions are of use in combating dental caries, dental erosion and/or tooth wear.

15 Claims, No Drawings

(56) References Cited

U.S. PATENT DOCUMENTS

| | | |
|---|---|---|
| 2007/0183984 A1 | 8/2007 | Haas et al. |
| 2008/0187500 A1 | 8/2008 | Karlinsey |
| 2008/0221681 A1 | 9/2008 | Trieu et al. |
| 2009/0324516 A1 | 12/2009 | Muscle et al. |
| 2010/0291164 A1 | 11/2010 | Karlinsey |

FOREIGN PATENT DOCUMENTS

| | | |
|---|---|---|
| GB | 593777 | 10/1947 |
| JP | 2000245821 | 9/2000 |
| JP | 2003073182 | 3/2003 |
| JP | 2003093496 | 4/2003 |
| WO | 9840406 | 9/1998 |
| WO | WO-0237258 | 3/2002 |
| WO | 2007068062 | 6/2007 |

OTHER PUBLICATIONS

Dushkin, "Potential of Mechanochemical Technology in Organic Synthesis and Synthesis of New Materials", Institute of Solid State Chemistry and Mechanochemistry, Siberian Branch of the Russian Academy of Sciences, UI. (Russia) Chemistry for Sustainable Development, vol. 12, 2004, pp. 251-273, XP002728802, http://www.sibran.ru/upload/iblock/4a3/4a30bb11b1f14.

Kim, et al., "Bioactive Organic-Inorganic Composite Prepared by Mechanochemical Method", Key Engineering Materials, Trans Tech Publications Ltd., Stafa-Zurich, CH, vol. 218-220, No. Bioceramics-14, Jan. 1, 2002, pp. 295-298, XP009127712, ISSN: 1013-9826, p. 296.

Busch, "Regeneration of Human Tooth Enamel", Angewandte Chemie International Edition 2004:43(11); 1428-1431.

* cited by examiner

DENTAL COMPOSITION

CROSS-REFERENCE TO RELATED APPLICATIONS

This application is a continuation-in-part of and claims priority to co-pending utility patent application Ser. No. 11/701,210 filed Jan. 31, 2007 and published as U.S. Patent Pub. No. 2007/0178220; and to co-pending U.S. patent application Ser. No. 12/018,627, filed Jan. 23, 2008, which claimed priority to U.S. provisional patent application Ser. No. 60/888,354, filed Feb. 6, 2007, U.S. provisional patent application Ser. No. 60/891,849, filed Feb. 27, 2007, and U.S. provisional patent application Ser. No. 60/941,095, filed May 31, 2007.

TECHNICAL FIELD

The present novel technology relates generally to the field of chemistry and, more particularly, to a dental remineralizing composition containing calcium and fluoride.

BACKGROUND

Tooth mineral is composed predominantly of calcium hydroxyapatite, $Ca_{10}(PO_4)_6(OH)_2$, which may be partially substituted with anions such as carbonate or fluoride, and cations such as zinc or magnesium. Tooth mineral may also contain non-apatitic mineral phases such as octacalcium phosphate and calcium carbonate.

Tooth loss may occur as a result of dental caries, which is a multifactorial disease where bacterial acids such as lactic acid produce sub-surface demineralisation that does not fully remineralise, resulting in progressive tissue loss and eventually cavity formation. The presence of a plaque biofilm is a prerequisite for dental caries, and acidogenic bacteria such as *Streptococcus mutans* may become pathogenic when levels of easily fermentable carbohydrate, such as sucrose, are elevated for extended periods of time.

Even in the absence of disease, loss of dental hard tissues can occur as a result of acid erosion and/or physical tooth wear; these processes are believed to act synergistically. Exposure of the dental hard tissues to acid causes demineralisation, resulting in surface softening and a decrease in mineral density. Under normal physiological conditions, demineralised tissues self-repair through the remineralising effects of saliva. Saliva is supersaturated with respect to calcium and phosphate, and in healthy individuals saliva secretion serves to wash out the acid challenge, and raises the pH so as to alter the equilibrium in favour of mineral deposition.

Dental erosion (i.e. acid erosion or acid wear) is a surface phenomenon that involves demineralization, and ultimately complete dissolution of the tooth surface by acids that are not of bacterial origin. Most commonly the acid will be of dietary origin, such as citric acid from fruit or carbonated drinks, phosphoric acid from cola drinks and acetic acid such as from vinaigrette. Dental erosion may also be caused by repeated contact with hydrochloric acid (HCl) produced in the stomach, which may enter the oral cavity through an involuntary response such as gastroesophageal reflux, or through an induced response as may be encountered in sufferers of bulimia.

Tooth wear (i.e. physical tooth wear) is caused by attrition and/or abrasion. Attrition occurs when tooth surfaces rub against each other, a form of two-body wear. An often dramatic example is that observed in subjects with bruxism, a grinding habit where the applied forces are high, and is characterised by accelerated wear, particularly on the occlusal surfaces. Abrasion typically occurs as a result of three-body wear and the most common example is that associated with brushing with a toothpaste. In the case of fully mineralised enamel, levels of wear caused by commercially available toothpastes are minimal and of little or no clinical consequence. However, if enamel has been demineralised and softened by exposure to an erosive challenge, the enamel becomes more susceptible to tooth wear. Dentin is much softer than enamel and consequently is more susceptible to wear. Subjects with exposed dentin should avoid the use of highly abrasive toothpastes, such as those based on alumina. Again, softening of dentin by an erosive challenge will increase susceptibility of the tissue to wear.

Dentin is a vital tissue that in vivo is normally covered by enamel or cementum depending on the location i.e. crown versus root respectively. Dentin has a much higher organic content than enamel and its structure is characterised by the presence of fluid-filled tubules that run from the surface of the dentin-enamel or dentin-cementum junction to the odontoblast/pulp interface. It is widely accepted that the origins of dentin hypersensitivity relate to changes in fluid flow in exposed tubules, (the hydrodynamic theory), that result in stimulation of mechanoreceptors thought to be located close to the odontoblast/pulp interface. Not all exposed dentin is sensitive since it is generally covered with a smear layer; an occlusive mixture comprised predominantly of mineral and proteins derived from dentin itself, but also containing organic components from saliva. Over time, the lumen of the tubule may become progressively occluded with mineralised tissue. The formation of reparative dentin in response to trauma or chemical irritation of the pulp is also well documented. Nonetheless, an erosive challenge can remove the smear layer and tubule "plugs" causing outward dentinal fluid flow, making the dentin much more susceptible to external stimuli such as hot, cold and pressure. As previously indicated, an erosive challenge can also make the dentin surface much more susceptible to wear. In addition, dentin hypersensitivity worsens as the diameter of the exposed tubules increases, and since the tubule diameter increases as one proceeds in the direction of the odontoblast/pulp interface, progressive dentin wear can result in an increase in hypersensitivity, especially in cases where dentin wear is rapid.

Loss of the protective enamel layer through erosion and/or acid-mediated wear will expose the underlying dentin, and are therefore primary aetiological factors in the development of dentin hypersensitivity.

It has been claimed that an increased intake of dietary acids, and a move away from formalised meal times, has been accompanied by a rise in the incidence of dental erosion and tooth wear.

In view of this, oral care compositions which can help prevent dental erosion and tooth wear, in addition to dental caries, would be advantageous.

Oral care compositions comprising a source of fluoride ions have been known for many years for combating dental caries. Fluoride ions are known to inhibit plaque bacteria that can cause plaque acid. Fluoride ions are also known to enhance remineralisation and to decrease demineralisation of dental enamel, thereby strengthening dental enamel from acidic challenges.

In more recent years, oral care compositions comprising a source of fluoride ions have also been marketed for combating dental erosion. Some dentifrice compositions have been especially formulated to maximise both the availability of fluoride ions in the composition and their uptake by dental enamel, so to strengthen teeth from both dietary and plaque acidic challenges. It is suggested that such dentifrices suitably do not contain calcium salts.

Attempts have been made over many years to maximise the efficacy of fluoride ions, in strengthening dental enamel, by including a source of calcium and phosphate ions to supplement the natural remineralisation provided by such ions already present in saliva.

However, formulating a source of fluoride ions together with a calcium (phosphate) compound is technically challenging given that the presence of calcium ions together with a source of fluoride ions, can cause the precipitation of insoluble calcium fluoride, thereby significantly reducing the availability of fluoride in an oral care composition. Various solutions to this problem have been suggested including the incorporation of an antinucleating agent or an alkali metal phytate together with the calcium and fluoride ions or the separation of a calcium compound from a source of fluoride ions either by means of a physical barrier in a two phase aqueous composition or by formulating the ingredients in a single phase anhydrous system.

Known anti-carious remineralizing gels, toothpastes and dentifrices comprising from about 0.5 to 10% by weight of α-tricalcium phosphate, tetracalcium phosphate or monocalcium phosphate monohydrate, suitably present in a dry mixture to be reconstituted into a gel by the addition of water which may contain other components including a source of fluoride ions, so to prevent premature reaction of the calcium and fluoride ions.

Some oral care compositions comprise various partially water soluble calcium salts, such as calcium sulphate, together with a source of phosphate and fluoride ions. Such calcium salts are separated until use from the source of phosphate and fluoride ions either by being formulated in a single phase anhydrous system or by means of a physical barrier in a two phase aqueous composition. It is suggested that the oral care compositions preferably contain from about 0.05% to about 15.0% by weight, more preferably from about 0.10% to about 10.0% by weight of the calcium salt(s), from about 0.05% to about 15.0% by weight, more preferably from about 0.10 to about 10.0% by weight of the phosphate salt(s) and from about 0.01% to about 5.0%, more preferably from about 0.02% to about 2.0% by weight of the fluoride salt(s).

Other oral care compositions comprise low quantities (i.e. from 0.01 to 0.09% by weight of the composition) of various sparingly soluble rod-shaped nanoparticulate calcium compounds such as hydroxyapatite, fluorapatite or calcium fluoride. It is suggested that such compositions can also contain other calcium compounds, which need not be nanoparticulate, such as calcium glycerophosphate, or calcium containing abrasives such as chalk, calcium pyrophosphate or dicalcium phosphate dihydrate. Such compositions can also comprise a source of fluoride ions, preferably in an amount of 0.01 to 0.2% by weight.

There are oral care compositions that comprise nanoparticulate calcium fluoride for combating dental erosion and/or tooth wear. The nanoparticulate calcium fluoride may be present in an amount of 0.001 to 20.0% by weight of the total composition, suitably from 0.01 to 10%, for example from 0.1 to 5.0% by weight of the total composition. It is stated that the oral care composition may further comprise a source of soluble fluoride ions, which can be present in an amount to provide from 25 to 3500 ppm, preferably from 100 to 1500 ppm of fluoride ions.

There are known in the art anti-cariogenic oral hygiene compositions that comprise calcium glycerophosphate and from 0.08 to 7.6% by weight of sodium monofluorophosphate, the sodium monofluorophosphate and the calcium glycerophosphate being present in the composition in a weight ratio of 10:1 to 3:1.

Accordingly, there remains an electrochemically driven problem with fluoride easily bonding with calcium to form calcium fluoride, effectively removing both calcium and fluoride from bioavailability. The present novel technology addresses this need.

SUMMARY

Accordingly, in a first aspect, the present novel technology provides an aqueous homogeneous oral care composition comprising a fluoride salt and unfunctionalised β-tricalcium phosphate, characterised in that β-tricalcium phosphate is present in a catalytic and fluoride-stable amount relative to the fluoride salt.

Without wishing to be bound by theory, it is believed that a catalytic amount of unfunctionalised β-tricalcium phosphate can act as a nucleating template or seed, thereby enhancing the efficacy of fluoride, together with calcium and phosphate ions naturally present in saliva, in remineralising dental enamel.

DETAILED DESCRIPTION

For the purposes of promoting an understanding of the principles of the novel technology, reference will now be made to the embodiments illustrated in the drawings and specific language will be used to describe the same. It will nevertheless be understood that no limitation of the scope of the novel technology is thereby intended, such alterations and further modifications in the illustrated device, and such further applications of the principles of the novel technology as illustrated therein being contemplated as would normally occur to one skilled in the art to which the novel technology relates.

By "aqueous homogeneous preparation" is meant that the oral care composition comprises water as an excipient and that all ingredients of the oral care composition are combined in one mixture; i.e. they are not kept apart in separate compartments or by means of an anhydrous carrier.

By "catalytic and fluoride-stable amount" is meant an amount sufficient to enhance the efficacy of fluoride in strengthening dental enamel from acidic challenges but not sufficient to compromise the long term storage stability of fluoride ions in the oral care composition.

It has now been discovered that unfunctionalised β-tricalcium phosphate is compatible with a source of fluoride ions in an aqueous homogeneous oral care composition, providing the unfunctionalised β-tricalcium phosphate is used in a low enough amount relative to the amount of fluoride ions present.

However, using unfunctionalised β-tricalcium phosphate in such a low amount relative to the source of fluoride ions would not necessarily be expected to augment the natural remineralisation provided by calcium and phosphate ions already present in saliva.

It has further been discovered that such low amounts of β-tricalcium phosphate can enhance the efficacy of fluoride in strengthening dental enamel from acidic challenges. The present novel technology is therefore based upon the two-fold discovery that a fluoride salt can be combined together with unfunctionalised β-tricalcium phosphate in a single phase aqueous oral care composition providing that β-tricalcium phosphate is present in a catalytic and fluoride-stable amount relative to the fluoride salt, so to enhance fluoride efficacy but not to compromise long term storage stability of the fluoride in the composition.

The minimum amount of a β-tricalcium phosphate that can be present relative to the amount of fluoride salt in an oral care composition, to enhance fluoride efficacy, can be determined by adding decreasing amounts of β-tricalcium phosphate d to a fixed amount of a fluoride salt and determining the relative efficacy of the oral care compositions (with and without β-tricalcium phosphate) in strengthening dental enamel using a variety of methods, such as surface microhardness measurements as shown in Examples 1 and 2.

The maximum amount of β-tricalcium phosphate that can be present relative to the amount of fluoride salt in an oral care composition, without compromising fluoride stability, can be determined by adding increasing amounts of β-tricalcium phosphate to a fixed amount of a fluoride salt and measuring the levels of available fluoride over time using accelerated aging conditions, as shown in Examples 3 and 4. A composition is deemed to have acceptable fluoride stability if the levels of available fluoride are no less than 10% of the theoretical amount that should be present.

Suitable fluoride salts are those that directly provide free fluoride ions in the oral care composition, such as alkali metal fluorides (eg sodium or potassium fluoride) or stannous fluoride.

Excluded from this definition are salts that indirectly provide free fluoride ions, such as sodium monofluorophosphate, which is hydrolyzed by salivary enzymes in the mouth, releasing free fluoride in situ. Sodium monofluorophosphate has previously been used in aqueous oral care compositions comprising ingredients, such as calcium compounds, which are incompatible with free fluoride ions, especially on long term storage. The present novel technology, however, avoids the need to use such a salt, and instead has found an elegantly simple way of formulating β-tricalcium phosphate with a salt directly providing free fluoride ions.

A preferred fluoride salt is sodium fluoride.

The fluoride salt is generally present in an amount to provide from 10 to 5000 ppm, eg from 25 to 3500 pm of fluoride ions, preferably from 100 to 1500 ppm, for example the composition may contain 0.1 to 0.5% by weight of sodium fluoride, eg 0.205% by weight (equating to 927 ppm of fluoride ions), 0.2542% by weight (equating to 1150 ppm of fluoride ions) or 0.315% by weight (equating to 1426 ppm of fluoride ions).

By "unfunctionalised β-tricalcium phosphate" is meant β-tricalcium phosphate that is not functionalised in the manner described in the parent applications.

Suitably β-tricalcium phosphate is used alone or in conjunction with fluorapatite.

Suitable amounts of β-tricalcium phosphate can readily determined by assessing the fluoride stability and relative fluoride efficacy of the oral care compositions according to the methods described in the Examples.

Suitably the weight ratio of fluoride ions to total calcium ions present in the oral care composition of the present novel technology ranges from about 2:1 to 100:1, suitably from 2.5:1 to 50:1, more suitably from 3:1 to 40:1, preferably from 3.5:1 to 30:1.

By total calcium ions is meant all the calcium ions provided by the calcium compound, both dissolved and undissolved in the oral care composition.

Unlike the aqueous compositions which may comprise solubilised calcium, phosphate and fluoride ions, the compositions of the present novel technology do not require, and suitably do not contain, an alkali metal phytate or an antinucleating agent.

Compositions of the present novel technology may further comprise one or more active agents conventionally used in oral healthcare compositions, for example, a desensitising agent, an anti-erosion agent, an anti-plaque agent; an anti-calculus agent, a whitening agent, an oral malodour agent, anti-inflammatory agent, an anti-oxidant, anti-fungal or wound healing agent or a mixture of at least two thereof. Such agents may be included at levels to provide the desired therapeutic effect.

Compositions of the present novel technology may comprise a desensitising agent, for combating dentin hypersensitivity. Examples of desensitising agents include a tubule blocking agent or a nerve desensitising agent and mixtures thereof. Suitable desensitising agents include a strontium salt such as strontium chloride, strontium acetate or strontium nitrate or a potassium salt such as potassium citrate, potassium chloride, potassium bicarbonate, potassium gluconate and especially potassium nitrate.

A desensitising amount of a potassium salt is generally between 2 to 8% by weight of the total composition, for example 5% by weight of potassium nitrate can be used.

Compositions of the present novel technology may comprise an anti-erosion agent, for example a polymeric mineral surface active agent or a stannous, zinc or copper compound.

Compositions of the present novel technology will contain appropriate formulating agents such as abrasives, surfactants, thickening agents, humectants, flavouring agents, sweetening agents, opacifying or colouring agents, preservatives and water, selected from those conventionally used in the oral care composition art for such purposes.

Compositions of the present novel technology are typically formulated in the form of toothpastes, sprays, mouthwashes, or gels.

Compositions of the present novel technology may be prepared by admixing the ingredients in the appropriate relative amounts in any order that is convenient and if necessary adjusting the pH to give a desired value, for example from 5.5 to 9.0

The pH is measured when the composition is slurried with water in a 1:3 weight ratio of the composition to water.

The present novel technology also provides a method of combating dental erosion and/or tooth wear which comprises applying an effective amount of a composition as hereinbefore defined to an individual in need thereof.

The present novel technology also provides a method of combating dental and/or root caries which comprises applying an effective amount of a composition as hereinbefore defined to an individual in need thereof.

The present novel technology also provides a method of combating dentin hypersensitivity which comprises applying an effective amount of a composition as hereinbefore defined to an individual in need thereof.

Generally, the present novel technology relates to an aqueous homogeneous oral care composition comprising a fluoride salt and a catalytic and fluoride-stable amount of β-tricalcium phosphate. The β-tricalcium phosphate is present in an amount sufficient to increase the efficacy of fluoride ions in strengthening dental enamel of teeth against acidic challenges, whilst not significantly compromising the long term storage stability of the fluoride ions in the oral care composition. Such compositions are of use in combating (i.e. helping to prevent, inhibit and/or treat) dental erosion and/or tooth wear. Such compositions are of use in combating dental and/or root caries. Such compositions are of use in combating dentin hypersensitivity.

The novel technology is further illustrated by the following Examples.

Example 1

20-Day pH Cycling Protocol, Surface and Cross-Sectional Microhardness and Enamel Fluoride Uptake Results In Vitro Anti-Caries Study White-spot lesions were produced in bovine enamel cores using conventional methods and then organized into the following groups (N=12):
1. Distilled water
2. 1100 ppm F
3. 1100 ppm F+98 ppm β-TCP These groups were then subjected to a remineralization/demineralization pH cycling model for 20 days. The model includes two one-minute treatment periods performed an hour apart in the morning, followed by one four-hour lactic acid-polyacrylic acid challenge, and finally two more one-minute treatment periods in the afternoon, administered daily for 10 days. In between the daily treatments and acid challenge, specimens were immersed in artificial saliva (AS). The treatments were diluted three-fold with distilled (DI) water (5 mL treatment solution:10 mL DI water). The treatments and saliva events were magnetically agitated at 300 rpm, while the acid challenge was static. After each treatment and acid challenge, the specimens were rinsed with DI water prior to placement into AS. Four fresh treatment slurries and fresh acid solution were used daily, with the artificial saliva solution changed once daily after the third treatment. Solution used for the acid challenge was the same as used to prepare the initial white-spot lesions.

After 20 days of cycling, the enamel specimens were examined for Vickers surface hardness (200 gf, 15 second dwell time). The change in Vickers hardness number (ΔVHN) was determined as the difference between the post and baseline values ($\Delta VHN = VHN_{post} - VHN_{base}$). These data are presented in Table 1.

Then, six enamel specimens were examined for cross-sectional surface microhardness (CSMH). A series of three indentation lanes per specimen are made under a load of 10 gf at 12.5 µm, 25 gf at 25 and 37.5 µm, and 50 gf at 50, 75, 100, 125 and 150 µm below the specimen surface. The Knoop indentation lengths were then converted to Knoop Hardness Numbers (KHN). Relative to KHN of sound enamel, relative lesions sizes in units of square root of KHN ($\sqrt{KHN}$) times enamel depth (µm) were then calculated using Simpson's Composite Rule. These data are presented in Table 2.

Enamel fluoride uptake (EFU) was determined for the remaining six specimens in units of micrograms of fluoride per unit enamel area (µg F/cm$^2$). The enamel specimens were immersed and continuously agitated in 0.5 ml of 1 N HClO$_4$ for 15 seconds. To determine fluoride concentration, 0.25 ml of this etchant was combined with 0.25 ml of 1 N NaOH and 0.5 ml of TISAB II. This solution was magnetically stirred, and a fluoride ion specific electrode was used to measure the free fluoride ion potential. These measurements were then converted to fluoride concentrations by using a fluoride electrode calibration curve constructed from known standards prepared with NaF. These data are presented in Table 3.

The microhardness and enamel fluoride uptake data were analyzed for normality using the Kolmogorov-Smirnov test with p=0.05. One-way analysis of variance (ANOVA) was performed to test for significant differences, followed by comparison tests at a 95% confidence level (p<0.05).

In summary, the addition of a low level of β-TCP to NaF solutions produced improved surface and subsurface benefits in white-spot enamel lesions. Additionally, remineralization benefits from this novel technology may be associated with or without increases in fluoride uptake.

Surface Microhardness Results:

TABLE 1

Summary of surface microhardness results after cycling through the 20-day cycling model.

| Group | VHN$^0$ | VHN$^{20}$ | ΔVHN$^{20}$ |
|---|---|---|---|
| Distilled Water | 35.8 (2.1) | 35.8 (2.4) | 0.0 (1.6) |
| 1100 ppm F | 35.6 (2.0) | 115.7 (3.2) | 84.2 (3.8) |
| 1100 ppm F + 98 ppm β-TCP | 35.6 (2.0) | 165.0 (3.2) | 128.9 (3.2) |

VHN$^0$ = mean baseline Vickers Hardness Number (VHN) and (SEM) (N = 12);

VHN$^{20}$ = mean VHN (SEM) (N = 12) after 20 days of cycling;

ΔVHN$^{20}$ = difference between mean VHN$^{20}$ (SEM) (N = 12) and VHN$^0$ after 20 days of cycling.

CSMH Results:

TABLE 2

Summary of cross-sectional microhardness (CSMH) after cycling through the 20-day remin/demin model.

| Group | ΔZ ($\sqrt{KHN} \cdot$ µm) |
|---|---|
| Distilled Water | 539.0 (27.4) |
| 1100 ppm F | 171.8 (24.6) |
| 1100 ppm F + 98 ppm β-TCP | 58.6 (23.5) |

ΔZ ($\sqrt{KHN} \cdot$ µm) = mean (SEM) lesion size (N = 6) after 20 days of cycling.

EFU Results:

TABLE 3

Summary of mean (SEM) enamel fluoride uptake (EFU) results from white-spot lesions (N = 6) after cycling.

| Group | EFU (µg F/cm$^2$) |
|---|---|
| Distilled Water | 0.4 (0.0) |
| 1100 ppm F | 2.9 (0.3) |
| 1100 ppm F + 98 ppm β-TCP | 2.2 (0.3) |

Example 2

20-Day pH Cycling Protocol, Surface Microhardness and Enamel Fluoride Uptake Results In Vitro Anti-Erosion Study Erosive lesions were produced in bovine enamel cores using 1% citric acid (pH=3.8) for 30 minutes and then organized into the following groups (N=12):

1. Distilled water
2. 1100 ppm F
3. 1100 ppm F+186 ppm β-TCP

These groups were then subjected to a remineralization/demineralization pH cycling model for 20 days. This model includes three two-minute treatment periods and five two-minute acid challenge periods. In between these events, the specimens are immersed in artificial saliva (AS). The treatments were diluted three-fold with distilled (DI) water (5 mL treatment solution:10 mL DI water). The treatment and AS systems were magnetically agitated at 300 rpm, while the acid challenge (0.3% citric acid, pH=3.8) was static. After each treatment and acid challenge, the specimens were rinsed with DI water prior to placement into the saliva mixture, which was changed once daily after the third acid challenge.

After 20 days of cycling, the enamel specimens were examined for Vickers surface hardness (200 gf, 15 second dwell time). The change in Vickers hardness number (ΔVHN) was determined as the difference between the post and baseline values ($\Delta VHN = VHN_{post} - VHN_{base}$). These data are presented in Table 4.

Enamel fluoride uptake was determined in units of micrograms of fluoride per unit enamel area (μg F/cm$^2$). Six enamel specimens were immersed and continuously agitated in 0.5 ml of 1 N HClO$_4$ for 15 seconds. To determine fluoride concentration, 0.25 ml of this etchant was combined with 0.25 ml of 1 N NaOH and 0.5 ml of TISAB II. This solution was magnetically stirred, and a fluoride ion specific electrode was used to measure the free fluoride ion potential. These measurements were converted to fluoride concentrations by using a fluoride electrode calibration curve constructed from known standards prepared with NaF. These data are presented in Table 5.

The microhardness and enamel fluoride uptake data were analyzed for normality using the Kolmogorov-Smirnov test with p=0.05. One-way analysis of variance (ANOVA) was performed to test for significant differences, followed by comparison tests at a 95% confidence level (p<0.05).

Surface Microhardness Results:

TABLE 4

Summary of surface microhardness results after cycling through an anti-erosion remin/demin model lasting 20 days.

| Group | VHN$^0$ | VHN$^{20}$ | ΔVHN$^{20}$ |
|---|---|---|---|
| Distilled Water | 214.6 (2.6) | 264.2 (3.3) | 49.2 (4.4) |
| 1100 ppm F | 214.5 (2.6) | 281.5 (3.7) | 67.7 (2.8) |
| 1100 ppm F + 186 ppm β-TCP | 214.7 (2.5) | 303.9 (3.4) | 89.3 (4.2) |

VHN$^0$ = mean baseline Vickers Hardness Number (VHN) and (SEM) (N = 12);
VHN$^{20}$ = mean VHN (SEM) (N = 12) after 20 days of cycling;
ΔVHN$^{20}$ = difference between mean VHN$^{20}$ (SEM) (N = 12) and VHN$^0$ after 20 days of cycling.

Enamel Fluoride Uptake Results:

TABLE 5

Summary of mean (SEM) enamel fluoride uptake (EFU) results from eroded enamel (N = 6) after cycling through an anti-erosion remin/demin model lasting 20 days.

| Group | EFU (μg F/cm$^2$) |
|---|---|
| Distilled Water | 2.7 (0.2) |
| 1100 ppm F | 3.2 (0.1) |
| 1100 ppm F + 186 ppm β-TCP | 3.7 (0.0) |

In summary, the addition of a low level of β-TCP to NaF solutions produced improved surface benefits, including microhardness and fluoride uptake in eroded enamel.

Example 3

Fluoride Stability

Fluoride availability was measured in triplicate for fluoride plus β-TCP. Solutions/suspensions of 0.24% NaF (1100 ppm F$^-$) plus β-TCP were prepared and stored at elevated conditions for 32 days at 40° C. Measurements were made using a fluoride-sensitive electrode and Accumet AR Dual Channel pH meter. TISAB II ionic strength adjuster was added in a 1:1 ratio with a sample volume (e.g. 5 ml), and standards were and measured in order to generate the calibration curve. Conversions from mV to ppm were determined based on the calibration curve and the data are presented in Table 6.

TABLE 6

Fluoride compatibility after accelerated aging conditions for 32 days at 40° C. in aqueous solutions of sodium fluoride.

| System | % NaF | Theoretical [F$^-$] | Measured [F$^-$] (Mean ± SD) | % of 1100 ppm F Control |
|---|---|---|---|---|
| Distilled Water | 0.0 | 0 ppm | 0.2 ± 0.0 ppm | 0.0% |
| 1100 ppm F | 0.24% | 1100 ppm | 1101.9 ± 0.0 ppm | 100.0% |
| 1100 ppm F + 98 ppm β-TCP | 0.24% | 1100 ppm | 1077.6 ± 2.4 ppm | 97.8% |
| 1100 ppm F + 186 ppm β-TCP | 0.24% | 1100 ppm | 1089.0 ± 7.4 ppm | 98.8% |

Example 4

30-, 60- and 90-Day Fluoride Stability with Low Levels of CaP Systems

Protocol:

Fluoride availability was measured in triplicate for the fluoride plus β-TCP combinations. Solutions/suspensions of 0.05% NaF (225 ppm F$^-$) plus β-TCP were prepared and stored at elevated conditions for 30, 60 and 90 days at 40° C. Measurements were made using a fluoride-sensitive electrode and Accumet AR Dual Channel pH meter. TISAB II ionic strength adjuster was added in a 1:1 ratio with a sample volume (e.g. 5 ml), and standards were and measured in order to generate the calibration curve. Conversions from mV to ppm were determined based on the calibration curve and the data are presented in Table 7, 8 and 9.

TABLE 7

30-day fluoride stability data at 40° C.

Concentration (in ppm ± standard deviation) of available fluoride [F—] after 30 days of accelerated aging (measured in triplicate):

| Compound | MW (g/mol) | % Ca | 5 ppm [Ca] | 15 ppm [Ca] | 25 ppm [Ca] | 40 ppm [Ca] | 50 ppm [Ca] | 60 ppm [Ca] |
|---|---|---|---|---|---|---|---|---|
| NaF | 42.0 | 0.0 | | | 221.2 (0.5) | | | |
| β-TCP | 310.2 | 38.7 | 209.8 (0.5) | 212.4 (0.5) | 210.7 (0.5) | 209.2 (0.9) | 213.3 (1.0) | 214.5 (0.0) |

TABLE 8

60-day fluoride stability data at 40° C.

Concentration (in ppm ± standard deviation) of available fluoride [F—] after 60 days of accelerated aging (measured in triplicate):

| Compound | MW (g/mol) | % Ca | 5 ppm [Ca] | 15 ppm [Ca] | 25 ppm [Ca] | 40 ppm [Ca] | 50 ppm [Ca] | 60 ppm [Ca] |
|---|---|---|---|---|---|---|---|---|
| NaF | 42.0 | 0.0 | | | 225.4 (0.9) | | | |
| β-TCP | 310.2 | 38.7 | 207.7 (0.0) | 208.2 (1.3) | 207.1 (1.3) | 209.1 (1.3) | 210.2 (0.9) | 209.1 (0.5) |

TABLE 9

90-day fluoride stability data at 40° C.

Concentration (in ppm ± standard deviation) of available fluoride [F—] after 90 days of accelerated aging (measured in triplicate):

| Compound | MW (g/mol) | % Ca | 5 ppm [Ca] | 15 ppm [Ca] | 25 ppm [Ca] | 40 ppm [Ca] | 50 ppm [Ca] | 60 ppm [Ca] |
|---|---|---|---|---|---|---|---|---|
| NaF | 410 | 0.0 | | | 226.5 (0.9) | | | |
| β-TCP | 310.2 | 38.7 | 207.7 (0.5) | 207.2 (0.5) | 206.3 (1.0) | 206.6 (0.8) | 207.4 (0.0) | 205.2 (0.5) |

Acceptable fluoride levels should lie within 10% of the theoretical at 30, 60, and 90 days. In consideration of the full range evaluated (5 ppm Ca to 60 ppm Ca), β-TCP provided sufficient availability over the range of the tested calcium concentrations.

β-TCP at a level of 5 ppm calcium ion provided good stability of fluoride present at 225 ppm, representing a fluoride ion to calcium ion ratio of 45:1.

β-TCP at a level of 15 ppm calcium ion provided good stability of fluoride present at 225 ppm, representing a fluoride ion to calcium ion ratio of 15:1.

β-TCP at a level of 25 ppm calcium ion provided good stability of fluoride present at 225 ppm, representing a fluoride ion to calcium ion ratio of 9:1.

β-TCP at a level of 40 ppm calcium ion provided good stability of fluoride present at 225 ppm, representing a fluoride ion to calcium ion ratio of 5.625:1.

β-TCP at a level of 50 ppm calcium ion provided good stability of fluoride present at 225 ppm, representing a fluoride ion to calcium ion ratio of 4.5:1.

β-TCP at a level of 60 ppm calcium ion provided good stability of fluoride present at 225 ppm, representing a fluoride ion to calcium ion ratio of 3.75:1.

While the novel technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the novel technology are desired to be protected.

I claim:

1. An aqueous oral care composition comprising:
   a fluoride salt portion; and
   an unfunctionalised β-tricalcium phosphate portion;
   wherein the β-tricalcium phosphate portion is present in a catalytic and fluoride-stable amount relative to the fluoride salt portion.

2. The composition according to claim 1, wherein the fluoride salt portion is selected from the group including alkali metal fluoride, stannous fluoride and combinations thereof.

3. The composition according to claim 2 wherein the fluoride salt portion is sodium fluoride.

4. The composition according to any one of claim 1 wherein fluoride salt portion and the β-tricalcium phosphate portion define a weight ratio of fluoride ions to total calcium ions and wherein the weight ratio ranges in value from 2:1 to 100:1.

5. The composition according to claim 4 wherein the weight ratio of fluoride ions to total calcium ions ranges from 2.5:1 to 50:1.

6. The composition according to claim 4 wherein the weight ratio of fluoride ions to total calcium ions ranges from 3:1 to 40:1.

7. The composition according to claim 4 wherein the weight ratio of fluoride ions to total calcium ions ranges from 3.5:1 to 30:1.

8. The composition according to claim 1 and further comprising a fluorapatite portion.

9. The composition according to claim 1 and further comprising a desensitising agent.

10. The composition according to claim 9 wherein the desensitising agent is selected from the group including a strontium salt, a potassium salt, and combinations thereof.

11. The composition according to claim 1 and further comprising an anti-erosion agent.

12. The composition according to claim 11 wherein the antierosion agent is selected from the group including abrasives, surfactants, thickening agents, humectants, flavoring agents, sweetening agents, opacifying agents, coloring agents, preservatives, and combinations thereof.

13. The composition according to claim 1 and further comprising a matrix material, wherein the matrix material is selected from the group including toothpastes, sprays, mouthwashes, gels, and combinations thereof.

14. A composition for increasing the efficacy of fluoride ions in strengthening dental enamel, comprising:
a first amount of water;
a second amount of fluoride salt dispersed in the water; and
a third amount of unfunctionalized β-tricalcium phosphate dispersed in the water;
wherein the first amount is substantially greater than the second and third amounts; and
wherein the second amount is substantially greater than the third amount.

15. The composition of claim 14 wherein the second amount of fluoride salt and the third amount of unfunctionalized β-tricalcium phosphate are dissolved in the first amount of water.

* * * * *